(12) United States Patent
Deshpande

(10) Patent No.: US 9,055,951 B2
(45) Date of Patent: Jun. 16, 2015

(54) ENDOVASCULAR TISSUE REMOVAL DEVICE

(75) Inventor: Manish Deshpande, Canton, MA (US)

(73) Assignee: Covidien LP, Mansfield, MA (US)

( * ) Notice: Subject to any disclaimer, the term of this patent is extended or adjusted under 35 U.S.C. 154(b) by 1059 days.

(21) Appl. No.: 13/113,187

(22) Filed: May 23, 2011

(65) Prior Publication Data
US 2012/0303022 A1 Nov. 29, 2012

(51) Int. Cl.
 A61B 18/14 (2006.01)
 A61B 18/00 (2006.01)

(52) U.S. Cl.
 CPC ... *A61B 18/1492* (2013.01); *A61B 2018/00285* (2013.01); *A61B 2018/00422* (2013.01); *A61B 2018/1472* (2013.01); *A61B 2218/002* (2013.01); *A61B 2218/007* (2013.01)

(58) Field of Classification Search
 USPC ............ 606/32, 33, 41, 48–50; 607/101–105
 See application file for complete search history.

(56) References Cited

U.S. PATENT DOCUMENTS

| | | | |
|---|---|---|---|
| 4,636,195 A | 1/1987 | Wolinsky | |
| 4,857,046 A | 8/1989 | Stevens et al. | |
| 5,098,431 A | 3/1992 | Rydell | |
| 5,419,767 A | 5/1995 | Eggers | |
| 5,462,529 A | 10/1995 | Simpson et al. | |
| 5,833,650 A | 11/1998 | Imran | |
| 5,947,985 A | 9/1999 | Imran | |
| 6,015,420 A | 1/2000 | Wulfman et al. | |
| 6,063,069 A | 5/2000 | Cragg et al. | |
| 6,096,054 A | 8/2000 | Wyzgala et al. | |
| 6,102,046 A | 8/2000 | Weinstein | |
| 6,126,635 A | 10/2000 | Simpson et al. | |
| 6,135,991 A | 10/2000 | Muni et al. | |
| 6,156,048 A | 12/2000 | Wulfman et al. | |
| 6,165,172 A * | 12/2000 | Farley et al. | 606/33 |
| 6,179,824 B1 * | 1/2001 | Eggers et al. | 604/500 |
| 6,203,561 B1 | 3/2001 | Ramee et al. | |
| 6,258,061 B1 | 7/2001 | Drasler et al. | |
| 6,258,109 B1 | 7/2001 | Barry et al. | |
| 6,273,876 B1 | 8/2001 | Klima et al. | |
| 6,290,689 B1 | 9/2001 | Delaney et al. | |
| 6,299,623 B1 | 10/2001 | Wulfman | |
| 6,416,526 B1 | 7/2002 | Wyzgala et al. | |
| 6,419,673 B1 | 7/2002 | Edwards et al. | |
| 6,451,037 B1 | 9/2002 | Chandrasekaran et al. | |
| 6,454,741 B1 | 9/2002 | Muni et al. | |

(Continued)

FOREIGN PATENT DOCUMENTS

| CA | 2318891 | 8/1999 |
|---|---|---|
| CA | 2652546 | 11/2007 |

(Continued)

OTHER PUBLICATIONS

European Search Report EP12181383 dated Jan. 25, 2013.

(Continued)

*Primary Examiner* — Michael Peffley
(74) *Attorney, Agent, or Firm* — Thomas M. Johnston, Esq.

(57) ABSTRACT

A monopolar electrosurgical apparatus is disclosed which includes a tissue removal device having electrical, mechanical and chemical tissue removal capabilities. The device can be operated to use any of its tissue removal capabilities alone or in combination with one or more of the other capabilities.

24 Claims, 4 Drawing Sheets

(56) References Cited

U.S. PATENT DOCUMENTS

| | | |
|---|---|---|
| 6,482,216 B1 | 11/2002 | Hiblar et al. |
| 6,485,500 B1 | 11/2002 | Kokish et al. |
| 6,491,660 B2 | 12/2002 | Guo et al. |
| 6,503,261 B1 | 1/2003 | Bruneau et al. |
| 6,544,276 B1 | 4/2003 | Azizi |
| 6,569,146 B1 | 5/2003 | Werner et al. |
| 6,569,177 B1 | 5/2003 | Dillard et al. |
| 6,579,299 B2 | 6/2003 | McGuckin, Jr. et al. |
| 6,595,953 B1 | 7/2003 | Coppi et al. |
| 6,632,230 B2 | 10/2003 | Barry |
| 6,635,027 B1 | 10/2003 | Cragg et al. |
| 6,679,879 B2 * | 1/2004 | Shadduck ................ 606/41 |
| 6,685,718 B1 | 2/2004 | Wyzgala et al. |
| 6,818,001 B2 | 11/2004 | Wulfman et al. |
| 6,893,438 B2 | 5/2005 | Hall et al. |
| 6,932,776 B2 | 8/2005 | Carr |
| 6,984,239 B1 | 1/2006 | Drasler et al. |
| 6,997,925 B2 | 2/2006 | Maguire et al. |
| 7,410,486 B2 | 8/2008 | Fuimaono et al. |
| 7,429,261 B2 | 9/2008 | Kunis et al. |
| 2002/0007190 A1 | 1/2002 | Wulfman et al. |
| 2002/0058866 A1 | 5/2002 | Segner |
| 2005/0267467 A1 * | 12/2005 | Paul et al. ................ 606/41 |
| 2011/0046542 A1 | 2/2011 | Evans et al. |

FOREIGN PATENT DOCUMENTS

| | | |
|---|---|---|
| CA | 2770987 | 2/2011 |
| WO | WO91/01114 | 2/1991 |
| WO | WO96/29014 | 9/1996 |
| WO | WO 96/34569 | 11/1996 |
| WO | WO 98/56324 | 12/1998 |
| WO | WO2009/152467 | 12/2009 |

OTHER PUBLICATIONS

Partial European Search Report dated Oct. 10, 2012 for EP 12 16 7496.

Canadian Office Action dated Mar. 18, 2013 in copending Canadian Application No. 2,776,095.

* cited by examiner

FIG. 4  FIG. 4A

ENDOVASCULAR TISSUE REMOVAL DEVICE

BACKGROUND

1. Technical Field

The present disclosure relates to electrosurgical apparatus, system and methods. More particularly, the present disclosure relates to an endovascular tissue removal device.

2. Background of Related Art

Apparatus, as well as systems and methods, which use electrosurgical energy to maintain or create patency in a body vessel are well known in the art. Electrosurgical apparatus apply electrical energy, such as, radio frequency electrical current, microwave energy or resistive heating, to a surgical site to cut, ablate, coagulate or seal tissue.

Two types of electrosurgical apparatus include bipolar and monopolar apparatus. A bipolar electrosurgical apparatus typically includes a handheld device including both an active electrode and a return electrode. The return electrode is placed in close proximity to the active electrode such that an electrical circuit is formed between the two electrodes. In use, it is the intent that the application of electrical current be limited to the body tissue positioned between the active and return electrodes. In order to achieve this intent without causing unwanted charring of tissue at the surgical site or causing collateral damage to adjacent tissue, it is necessary to control the electrical output, such as by controlling the power, waveform, voltage, current, etc., from an electrosurgical generator.

A monopolar electrosurgical apparatus includes an active electrode which forms part of a handheld device of the electrosurgical apparatus and a return electrode which is located remotely from the handheld device and is configured to engage a patient to carry current back to an electrosurgical generator of the electrosurgical apparatus. Typically, the return electrode is a pad upon part of which the patient lies. Because the handheld device of a monopolar electrosurgical apparatus includes only an active electrode, the handheld device of the monopolar electrosurgical apparatus can be of simpler construction compared to the handheld device of a bipolar electrosurgical apparatus. However, monopolar devices typically are more difficult to control to limit collateral damage.

As understood in the art, certain types of occlusive tissue are more suitable to certain methods of removal. For example, chronic clots are not amenable to removal by using solely chemical agents such as tPA. In addition, a single clot may include multiple types of tissue. Since the morphology of occlusive tissue typically is not known prior to initiation of a removal procedure, it would be desirable to provide a tissue removal device having multiple tissue removal capabilities.

Accordingly, there exists a need in the art for a monopolar electrosurgical apparatus which includes a handheld device of simple construction which has a plurality of tissue removal capabilities effective in maintaining or creating patency in a partially or wholly occluded blood vessel, while limiting the area of tissue removal and collateral damage.

SUMMARY

The present disclosure relates to a monopolar electrosurgical system including an RF generator, a ground pad communicating with the RF generator and a tissue removal device comprising a catheter and a catheter insert positioned within the catheter. The catheter and the catheter insert define a fluid channel therebetween extending from a distal end of the catheter to a proximal end of the catheter. The catheter may also include a balloon which is expandable from a contracted state to an inflated state within the body vessel. A monopolar electrode is supported on a distal end of the catheter insert and is in electrical communication with the RF generator. The electrode may extend distally of the catheter and be positioned and configured to engage and mechanically breakup tissue.

In one embodiment, the electrode is substantially conically-shaped and includes a distally positioned apex positioned to engage tissue. Alternatively, the electrode may have a triangular shape which defines an apex for engaging tissue. The catheter insert may include a helical channel formed about an outer surface of the catheter insert, wherein the helical channel and the catheter define the fluid channel.

In one embodiment, the catheter insert has a fluted configuration and is positioned within the catheter to define the fluid channel. The electrode may also have a fluted configuration and is supported on a distal end of the catheter insert. A distal face of the electrode may define on abrasive surface to enhance the mechanical breakup of tissue.

In one embodiment, the catheter insert includes a guidewire bore.

The system can include a fluid suction/supply device adapted to releasably engage the tissue removal device such that the fluid suction/supply device is in fluid communication with the fluid channel and is operable to aspirate fluid from or supply fluid to a distal end of the tissue removal device through the fluid channel.

A source of pressurized fluid is provided which is in fluid communication with the balloon.

The present disclosure also relates to a tissue removal device which includes a catheter, a catheter insert positioned within the catheter, and a monopolar electrode supported on a distal end of the catheter insert. The electrode is positioned to extend distally of the catheter and is configured to engage and mechanically breakup tissue within a body vessel. The monopolar electrode is adapted to communicate with an RF generator or other source of energy.

In one embodiment, the catheter and the catheter insert define a fluid channel therebetween, which is configured to provide aspiration at the distal end of the catheter and to supply fluid to the distal end of the catheter.

In one embodiment, the catheter includes a balloon positioned proximally of the monopolar electrode which is movable from a contracted state to an inflated state.

The present disclosure also relates to a tissue removal device including an outer catheter having an open end and a first expandable balloon positioned proximally of the open end. A catheter extends through the open end of the outer catheter and defines a fluid supply channel. The catheter insert also includes a second distally positioned expandable balloon and at least one outlet port in fluid communication with the fluid supply channel positioned between the first and second expandable balloons. At least one electrode is positioned on an outer surface of the outer catheter distally of the first expandable balloon and is positioned to engage tissue within a body wall. In one embodiment, the at least one electrode includes a plurality of longitudinally extending electrodes spaced about the catheter wherein the at least one electrode projects radially outward from the outer surface of the outer catheter.

BRIEF DESCRIPTION OF THE DRAWINGS

Various embodiments of the present disclosure are described herein with reference to the drawings wherein:

FIG. 4 is a front end view of the handheld device of the monopolar electrosurgical apparatus shown in FIG. 1;

FIG. 4A is a cross-sectional view taken along section lines 4A-4A of FIG. 2.

DESCRIPTION OF THE EMBODIMENTS

Figure 1:
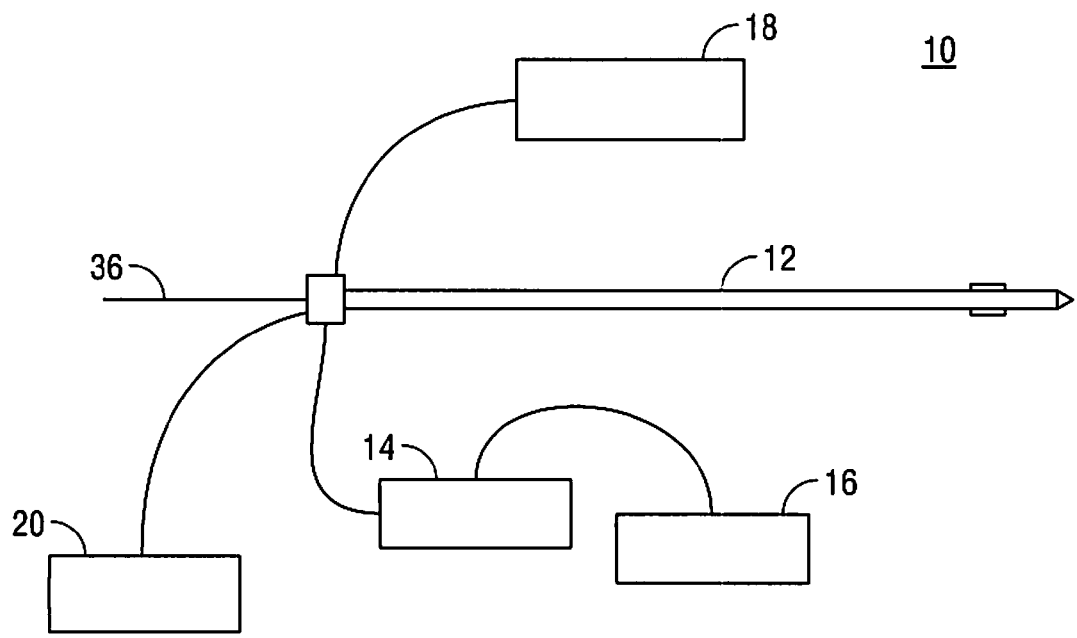
FIG. 1 is a schematic view of one embodiment of the presently disclosed monopolar electrosurgical apparatus.

Embodiments of the presently disclosed endovascular tissue removal device will now be described in detail with reference to the drawings wherein like reference numerals identify similar or identical elements. As used herein, the term "distal" refers to that portion of the device which is furthest from the user while the term "proximal" refers to that portion of the device which is closer to the user. In the following description, well known functions or constructions are not described in detail to avoid obscuring the present disclosure in unnecessary detail.

FIG. 1 is a schematic illustration of a monopolar electrosurgical system 10 according to one embodiment of the present disclosure. The system 10 includes a tissue removal device 12, an RF generator 14, a ground pad 16, a pressurized source of fluid 18, and a fluid suction/supply device 20. Referring also to FIGS. 2-5, the tissue removal device 12 includes an outer catheter 22 and a catheter insert 24. Catheter insert 24 is dimensioned to be received within catheter 22 in a fluid tight manner. A helical channel 26 is defined along an outer surface of catheter insert 24. The helical channel 26 defines a fluid channel 26a which is positioned between an inner wall of catheter 22 and catheter insert 24. The fluid channel 26a communicates with the fluid suction/supply device 20 via a cavity 27 (FIG. 5) defined in a proximal end of the catheter 22 such that fluid can be supplied to or withdrawn from the distal end of catheter 22 via fluid channel 26a.

Figure 4B:
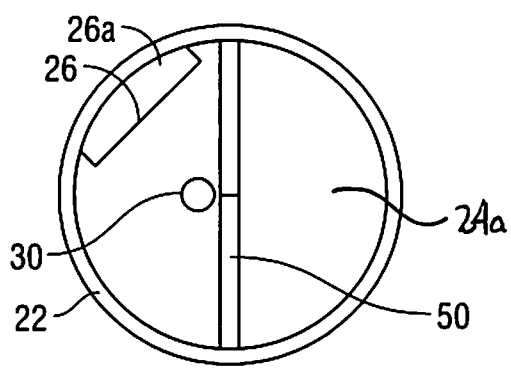
FIG. 4B is front end view of an example in which an electrode may have a conical configuration.
Figure 4B:
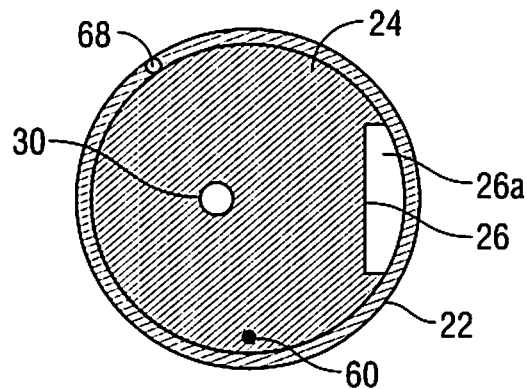
Figure 4B:
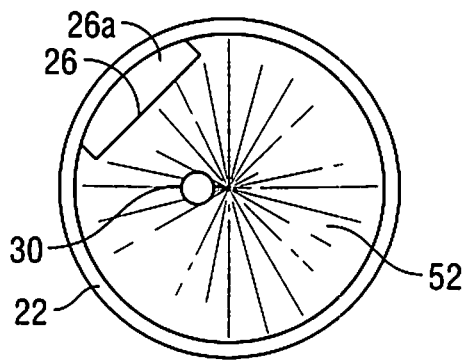
Figure 5:
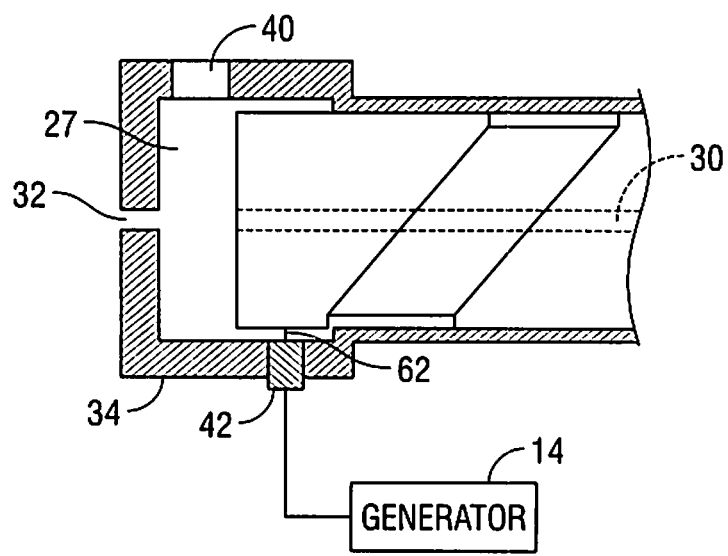
FIG. 5 is a side cross-sectional view of the handheld device of the monopolar electrosurgical apparatus shown in FIG. 1.

Referring also to FIGS. 4-5, catheter insert 24 is fixedly secured within catheter 22 using known attaching means, e.g., adhesives, pins, friction, or the like. Alternatively, catheter insert 24 can be movably positioned within catheter 22 to facilitate movement, e.g., rotation, of catheter insert 24 with respect to catheter 22. A guidewire bore 30 extends through the catheter insert 24 from a proximal end of the catheter insert 24 to the distal end of the catheter insert 24. The proximal end of catheter 22 includes a hub 34 (FIG. 5) which defines an opening 32 which is aligned with guidewire bore 30 to facilitate insertion of a guidewire 36 (FIG. 1) into bore 30. The distal end of guidewire bore 30 may be positioned offset from the longitudinal axis of catheter insert 24 such that the guidewire 36 does not pass through the apex 52 of electrode 50 as discussed below. See FIG. 4. Although not shown, the proximal end of bore 30 and/or hub opening 32 may include a seal or flap valve to prevent fluid from entering guidewire bore 30 or hub opening 32 prior to and/or while guidewire 36 is positioned in bore 30. The distal end of catheter insert 24 includes a conical tip 24a. Alternatively, the distal end of catheter insert 24 may be flat or have any of a variety of configurations.

Referring to FIG. 5, hub 34 of catheter 30 includes a port 40 for fluidly connecting cavity 27 to the fluid suction/supply device 20. Although not shown, port 40 may be configured to releasably engage a medical device, e.g., port 40 may include a luer-type connector for releasably engaging a fluid suction/supply device, such as a syringe. In addition, hub 34 also includes a connector 42 for electrically connecting RF generator 14 to catheter insert 24 as will be discussed in further detail below.

Figure 2:
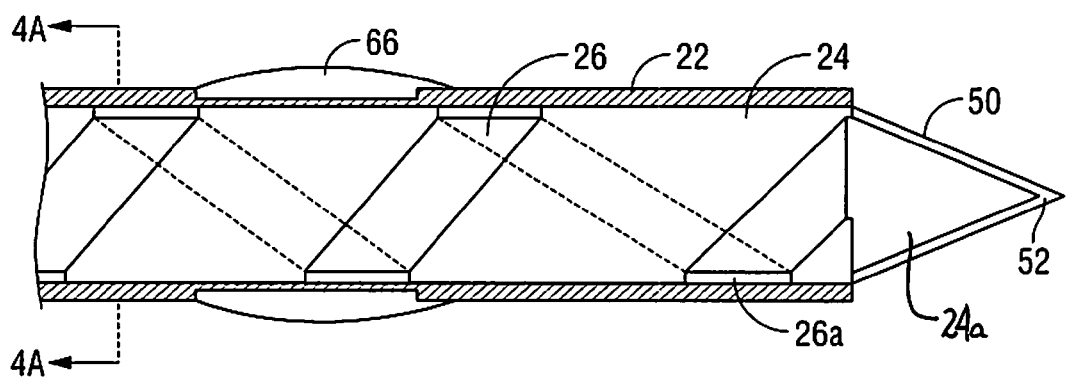
FIG. 2 is an enlarged side cross-sectional view of the distal end of the handheld device of the monopolar electrosurgical apparatus shown in FIG. 1.
Figure 3:
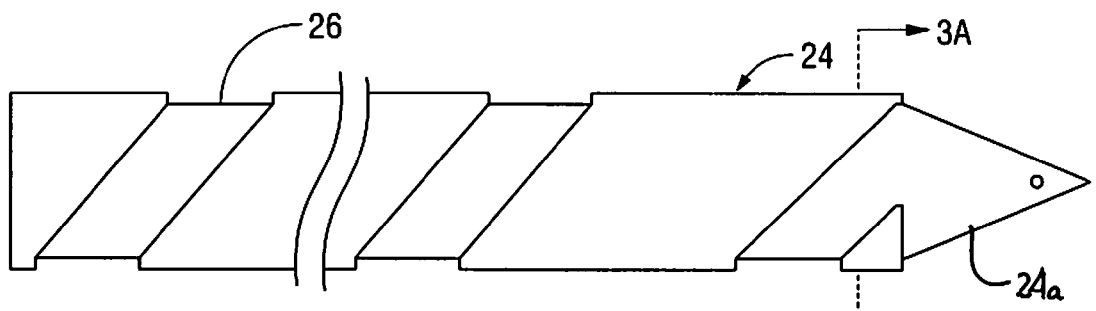
FIG. 3 is a side view of the catheter insert of the handheld device of the monopolar electrosurgical apparatus shown in FIG. 1.
Figure 3A:
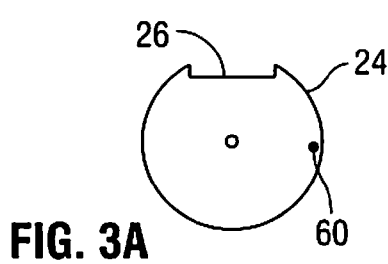
FIG. 3A is a front end view of the catheter insert shown in FIG. 1.

Referring to FIG. 2, an electrode 50 is supported on the distal end of catheter insert 24. In one embodiment, electrode 50 has a substantially triangular configuration with a distally positioned apex 52. Alternatively, as shown in FIG. 4B, the electrode may have a conical configuration and be positioned over the conical tip 24a of catheter insert 24. Alternatively, other electrode configurations are envisioned. The electrode 50 including apex 52 is configured to enhance the breakup or dislodging of tissue within a vessel. The electrode 50 is electrically connected to the RF generator 14 by an electrical conductor 60 extending along or through the catheter insert 24, e.g., wire 60 (FIG. 4A). The proximal end of electrical conductor 60 is connected to connector 42 by a second electrical connector 62 (FIG. 5).

Referring again to FIG. 2, in one embodiment, the distal end of the catheter 22 includes a balloon 66, for example, a centration balloon. Balloon 66 communicates with a source of pressurized fluid 18 via a channel 68 (FIG. 4A) to facilitate movement of the balloon 66 from a contracted state to an expanded state. In the expanded state, the centration balloon 66 centers catheter 22 within a vessel to center electrode 50 within the vessel. By centering the electrode within a vessel, the spacing between the electrode 50 and a vessel wall can be controlled to prevent inadvertent damage to the vessel wall. In some embodiments, a spacing of 1.5 mm to about 2 mm between electrode 50 and the vessel wall is desired to prevent damage to the vessel wall.

In one embodiment, electrode 50 is secured to the distal end of catheter insert 24 using an adhesive. Alternatively, the electrode 50 may be secured to the distal end of catheter insert 24 by overmolding, electrodeposition, crimping or the like.

Catheter 22 and/or catheter insert 24 may be formed from a synthetic resin, such as a polyurethane or similar material. Alternatively, catheter 22 and/or catheter insert 24 may be formed from a softer elastomeric material such as silicone. The assembled catheter 22 and catheter insert 24 should have sufficient pliability to be insertable into a body vessel, yet be sufficiently rigid to be capable of applying pressure on a vessel occlusion as will be discussed below.

In use, the tissue removal device 12 is positioned within a partially occluded or occluded vessel such that apex 52 of the electrode 50 is positioned adjacent the occlusion. Placement of the device 12 within a vessel can be achieved by first positioning guidewire 36 within the vessel using, for example, a needle cannula (not shown) in a known manner. After the guidewire 36 is positioned within the vessel and advanced to the desired location adjacent the occlusion, the tissue removal device 12 is slid over the guidewire 36 by positioning guidewire 36 within guidewire bore 30 and sliding tissue removal device 12 over the guidewire 36 into the body vessel. A dilator/sheath assembly (not shown) may be used to facilitate insertion of tissue removal device 12 into the body vessel to the desired location. Thereafter, guidewire 36 can be removed from tissue removal device 12.

If the tissue removal device 12 includes a centration balloon 66, the centration balloon 66 can be inflated to its inflated state to center the catheter 22 and electrode 50 within the body vessel. Typically, the balloon 66 is only partially inflated so as not to contact the vessel walls and occlude flow through the vessel. Thereafter, the RF generator 14 is activated to power the electrode 50. After the electrode 50 is powered, the electrode 50 is advanced into contact with the occlusion to melt, soften or breakup the occlusion and thereafter, pass through the occlusion. As this occurs, the tissue can be aspirated from the site of the occlusion via the fluid channel 26a using the fluid suction/supply device 20. In addition to the removal of tissue due to electrical power of the electrode 50, the configuration of electrode 50 can also be used to mechanically assist in the removal of tissue. More specifically, catheter 22 can be advanced and rotated manually to advance and rotate electrode 50 in relation to the occlusion to mechanically breakup or dislodge the tissue defining the occlusion. As discussed above, the electrode 50 may have an apex 52 or pointed distal end to facilitate the mechanical breakup and removal of tissue. Other electrode configurations for enhancing the mechanical breakup of an occlusion are envisioned.

In addition to the electrical and mechanical tissue removal methods discussed above, tissue removal device 12 may also be used to supply a traditional thrombolytic agent or a tissue plasminogen activator (tPA) to chemically remove or assist in the removal of the tissue defining the occlusion.

Figure 6:
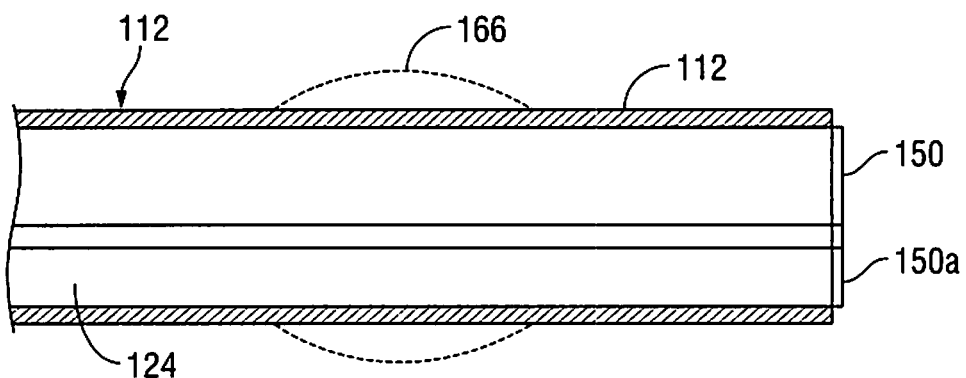
FIG. 6 is a side cross-sectional view of another embodiment of a handheld device of the presently disclosed monopolar electrosurgical apparatus.
Figure 6A:
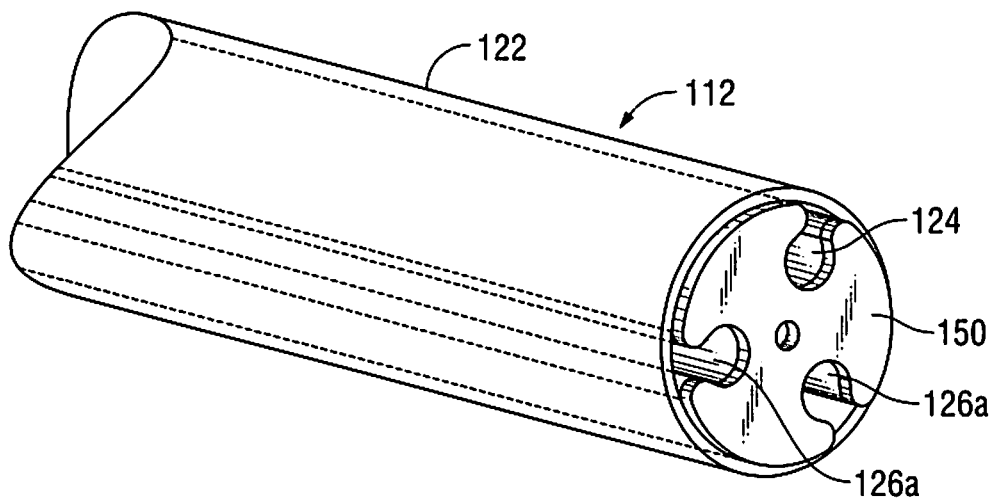
FIG. 6A is a side perspective view from the front end of the handheld device shown in FIG. 6.

FIGS. 6 and 6A illustrate the distal end of an alternative embodiment of the presently disclosed tissue removal device shown generally as 112. Tissue removal device 112 is similar to tissue removal device 12 except that configuration of the catheter insert 124 and the electrode 150 of tissue removal device 112 differ from the catheter insert 24 and electrode 50 of tissue removal device 12. More specifically, the tissue removal device 112 includes a catheter 122, a catheter insert 124 and an electrode 150. Device 112 may also include a centration balloon 166. The catheter insert 124 and the electrode 150 each have a fluted configuration which define a plurality of fluid channels 126a with the catheter 122. The electrode 150 is secured to a distal face of the catheter insert 124 in any suitable manner, such as by adhesives, overmolding or the like. The face 150a of electrode 150 may be formed with an abrasive outer surface to assist in the mechanical breakup of the tissue defining the occlusion.

The placement and use of tissue removal device 112 is substantially the same as that described above with respect to tissue removal device 12. As such, no further discussion is provided herein.

Figure 7:
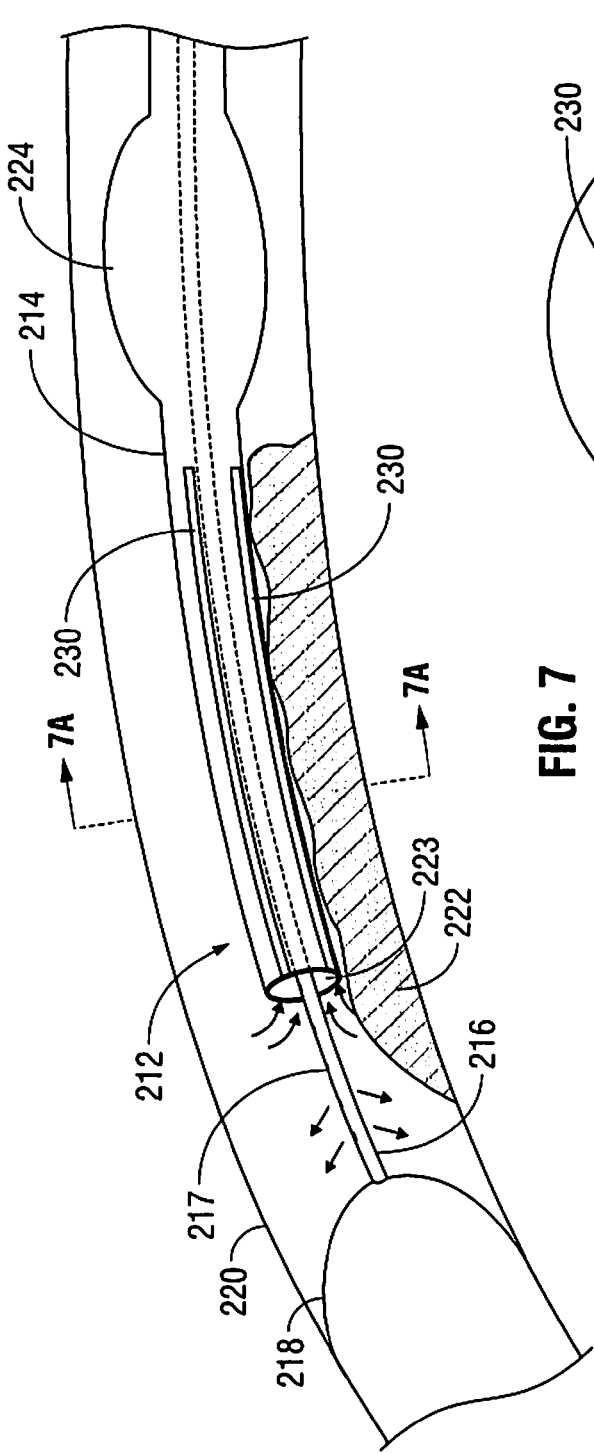
FIG. 7 is a side view of the distal end of another embodiment of the presently disclosed handheld device of a monopolar electrosurgical apparatus.
Figure 7A:
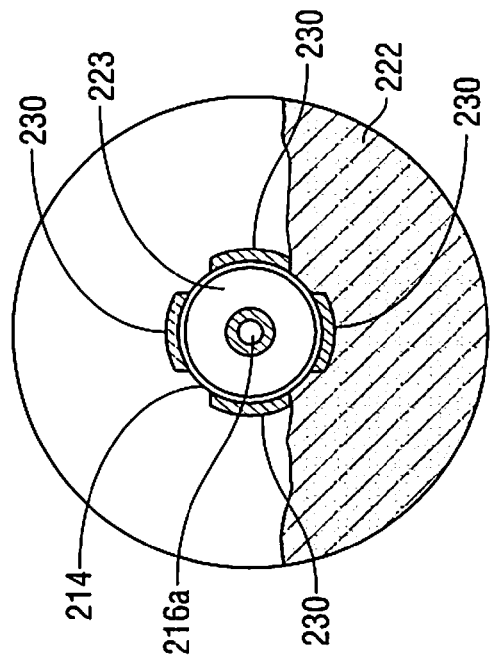
FIG. 7A is a cross-sectional view taken along section lines 7A-7A of FIG. 7.

FIGS. 7 and 7A illustrate the distal end of an alternative embodiment of the presently disclosed tissue removal device shown generally as 212. Tissue removal device 212 includes an outer catheter 214 and a catheter insert 216. Catheter insert 216 defines a fluid supply channel 216a and is positioned within and extends from the distal end of outer catheter 214. The distal end of catheter insert 216 includes a series of outlet ports 217 and a distally positioned balloon 218. Balloon 218 is expandable from a contracted state to an expanded state. In the expanded state, balloon 218 is moved into sealing engagement with the inner wall of a body vessel 220 to partially confine occlusive tissue 222 within the designated area of the body vessel 220.

Outer catheter 214 is positioned about catheter insert 216 to define a fluid aspiration channel 223. Outer catheter 214 includes a proximal balloon 224 which is movable from a contracted state to an expanded state. The proximal balloon 224 can be expanded to engage the inner wall of body vessel 220 to confine the occlusive tissue 222 between the distal balloon 218 and the proximal balloon 224 or, alternatively, the proximal balloon 224 can be partially expanded to center outer catheter 214 within the body vessel 220. A series of electrodes 230 are patterned about the surface of the distal end of the outer catheter 214. Although four electrodes 230 which extend along the longitudinal axis of the outer catheter 214 are illustrated in FIG. 7A, one or more electrodes 230 may be patterned on the outer surface of the outer catheter 214 in a variety of different orientations. Although not shown, electrodes 230 are in electrical communication with an RF generator or other energy source in a manner similar to that disclosed above with respect to electrode 50 of tissue removal device 12 (FIG. 2).

In use, after tissue removal device 212 is positioned within body vessel 220 adjacent occlusive tissue 222, distal balloon 218 is moved to the expanded state into engagement with an internal wall of body vessel 220 at a location distally of the occlusive tissue 222. Next, the proximal balloon 224 is expanded at a location proximal to the distal balloon 218 to center the outer catheter 214 within the body vessel 220. A chemical agent, such as a traditional thrombolytic agent or a tissue plasminogen activator, e.g., tPA, may be injected through fluid supply channel 216a of the catheter insert 216 through outlet ports 217 into the area between the distal balloon 218 and the proximal balloon 224 into contact with the occlusive tissue 222. Alternatively, saline or a saline solution may be supplied to the site of the occlusion through fluid supply channel 216a and aspirated with blood and tissue through the aspiration channel 223. Simultaneously, the outer catheter 214 is moved to position the electrodes 230 against the surface of the occlusive tissue 222 and also the source of energy, e.g., the RF generator, is activated to power the electrodes 230. The electrodes 230 function to electrically melt, soften, and/or breakup the occlusive tissue 222. In addition, movement of the electrodes 230 over the surface of the occlusive tissue 222 mechanically enhances the breakup or dislodging of the occlusive tissue 222, and contact of the occlusive tissue 222 with the chemical agent further assists in the breakup of the occlusive tissue 222. As shown in FIG. 7, the occlusive tissue 222 which is removed from body vessel 220 is aspirated through aspiration channel 223.

Each of the embodiments of the presently disclosed tissue removal device is capable of electrical, mechanical and/or chemical removal of occlusive tissue. As known in the art, certain types of occlusive tissue are more amenable to certain methods of removal. For example, chronic clots, as compared to acute clots, cannot be effectively removed using solely chemical agents such as tPA. Accordingly, the tissue removal capabilities of the presently disclosed tissue removal devices can be used alone or in combination with other capabilities to effectively remove occlusive tissue within a body vessel. For example, where the occlusive tissue is a chronic clot, the clot can be effectively removed using the electrical and mechanical capabilities of the tissue removal device.

Further, while the electrodes have been described as applying RF energy, the electrodes may apply other modes of energy, such as microwave, ultrasonic, or resistive heating.

Persons skilled in the art will understand that the devices and methods specifically described herein and illustrated in the accompanying drawings are non-limiting exemplary embodiments. It is envisioned that the elements and features illustrated or described in connection with one exemplarly embodiment may be combined with the elements and features of another without departing from the scope of the present disclosure. As well, one skilled in the art will appreciate further features and advantages of the system based on the above-described embodiments. Accordingly, the present disclosure is not to be limited by what has been particularly shown and described, except as indicated by the appended claims.

The invention claimed is:

1. A monopolar electrosurgical system comprising:
an RF generator;
a ground pad communicating with the RF generator; and
a tissue removal device comprising a catheter and a catheter insert positioned within the catheter, the catheter and the catheter insert defining a fluid channel therebetween extending from a distal end of the catheter to a proximal end of the catheter, the catheter including a balloon which is expandable from a contracted state to an inflated state, and further including a monopolar electrode in electrical communication with the RF generator and supported on a distal end of the catheter insert, the monopolar electrode comprising a pointed end, extending distally of the catheter, and being positioned and configured for the pointed end of the monopolar electrode to engage and mechanically breakup tissue.

2. The monopolar electrosurgical system according to claim 1, wherein the pointed end of the monopolar electrode includes a distally positioned apex positioned to engage tissue.

3. The monopolar electrosurgical system according to claim 2, wherein the catheter insert includes a helical channel formed about an outer surface of the catheter insert, the helical channel and the catheter defining the fluid channel.

4. The monopolar electrosurgical system according to claim 1, wherein the catheter insert has a fluted configuration, the catheter insert being positioned within the catheter to define the fluid channel.

5. The monopolar electrosurgical system according to claim 4, wherein the electrode has a fluted configuration and is supported on a distal end of the catheter insert.

6. The monopolar electrosurgical system according to claim 5, wherein a distal face of the electrode defines on abrasive surface.

7. The monopolar electrosurgical system according to claim 1, wherein the catheter insert includes a guidewire bore.

8. The monopolar electrosurgical instrument according to claim 1, further including a fluid handling device adapted to engage the tissue removal device, the fluid handling device being in fluid communication with the fluid channel and being operable to aspirate fluid from or supply fluid to a distal end of the tissue removal device through the fluid channel.

9. The monopolar electrosurgical system according to claim 1, further including a source of pressurized fluid in fluid communication with the balloon.

10. The monopolar electrosurgical system according to claim 1, wherein the electrode is conically shaped.

11. The monopolar electrosurgical system according to claim 1, wherein the electrode is triangular shaped.

12. A tissue removal device comprising:
a catheter;
a catheter insert positioned within the catheter; and
an electrode supported on a distal end of the catheter insert, the electrode comprising a pointed end, the electrode being positioned to extend distally of the catheter insert and being configured for the point end of the electrode to engage and mechanically breakup tissue within a body vessel, the electrode being adapted to communicate with a source of energy;
wherein the catheter and the catheter insert define a fluid channel therebetween, the fluid channel being configured to provide aspiration at the distal end of the catheter and to supply fluid to the distal end of the catheter.

13. The tissue removal device according to claim 12, wherein the pointed end of the electrode includes a distally positioned apex positioned to engage tissue.

14. The tissue removal device according to claim 13, wherein the catheter insert includes a helical channel formed about an outer surface of the catheter insert, the helical channel and the catheter defining the fluid channel.

15. The tissue removal device according to claim 12, wherein the catheter insert has a fluted configuration, the catheter insert being positioned within the catheter to define the fluid channel.

16. The tissue removal device according to claim 15, wherein the electrode has a fluted configuration which corresponds to the configuration of the catheter insert and is supported on a distal end of the catheter insert.

17. The tissue removal device according to claim 16, wherein the distal face of the electrode defines an abrasive surface.

18. The tissue removal device according to claim 12, wherein the catheter insert defines a guidewire bore.

19. The tissue removal device according to claim 12, wherein the catheter includes a balloon positioned proximally of the electrode, the balloon being movable from a contracted state to an inflated state.

20. The tissue removal device of claim 12, wherein the source of energy provides monopolar RF energy, sonic energy or resistive heating energy to the electrode.

21. A tissue removal device comprising:
an outer catheter defining an outer circumferential surface and having an open end and a first expandable balloon positioned proximally of the open end;
a catheter insert extending through the open end of the outer catheter and defining a fluid supply channel, the catheter insert including a second distally positioned expandable balloon and at least one outlet port in fluid communication with the fluid supply channel positioned between the first and second expandable balloons; and
at least one electrode positioned on the outer circumferential surface of the outer catheter distally of the first expandable balloon, the at least one electrode being positioned to engage tissue within a body wall.

22. The tissue removal device according to claim 21, wherein the at least one electrode includes a plurality of longitudinally extending electrodes spaced about the outer circumferential surface of the catheter.

23. The tissue removal device according to claim 21, wherein the at least one electrode projects radially outward from the outer circumferential surface of the outer catheter.

24. The tissue removal device according to claim 21, wherein the electrode is constructed to distribute monopolar RF, ultrasonic or resistive heating energy to tissue within a body wall.

* * * * *